(12) United States Patent
Mamedov

(10) Patent No.: US 10,669,218 B2
(45) Date of Patent: Jun. 2, 2020

(54) PROCESS FOR CATALYTIC OXIDATIVE DEHYDROGENATION OF ETHANE TO ETHYLENE IN THE PRESENCE OF CHLORINE INTERMEDIATES

(71) Applicant: Sabic Global Technologies, B.V., Bergen op Zoom (NL)

(72) Inventor: Aghaddin Mamedov, Sugar Land, TX (US)

(73) Assignee: Sabic Global Technologies, B.V., Bergen op Zoom (NL)

( * ) Notice: Subject to any disclaimer, the term of this patent is extended or adjusted under 35 U.S.C. 154(b) by 0 days.

(21) Appl. No.: 16/532,056

(22) Filed: Aug. 5, 2019

(65) Prior Publication Data

US 2019/0359546 A1 Nov. 28, 2019

Related U.S. Application Data

(63) Continuation of application No. PCT/US2018/016855, filed on Feb. 5, 2018.

(60) Provisional application No. 62/455,749, filed on Feb. 7, 2017.

(51) Int. Cl.
| | |
|---|---|
| *C07C 5/48* | (2006.01) |
| *B01J 23/34* | (2006.01) |
| *B01J 23/02* | (2006.01) |
| *C07C 11/04* | (2006.01) |
| *B01J 23/10* | (2006.01) |

(52) U.S. Cl.
CPC .......... *C07C 5/48* (2013.01); *B01J 23/10* (2013.01); *B01J 23/34* (2013.01); *C07C 11/04* (2013.01); *C07C 2521/04* (2013.01); *C07C 2521/10* (2013.01)

(58) Field of Classification Search
None
See application file for complete search history.

(56) References Cited

U.S. PATENT DOCUMENTS

| | | | | |
|---|---|---|---|---|
| 4,939,310 | A * | 7/1990 | Wade | C07C 2/84 |
| | | | | 585/500 |
| 5,157,188 | A | 10/1992 | Kolts et al. | |
| 5,321,185 | A | 6/1994 | van der Vaart | |
| 6,096,934 | A | 8/2000 | Rekoske | |
| 6,130,183 | A * | 10/2000 | Herskowitz | B01J 23/007 |
| | | | | 502/224 |
| 6,992,113 | B2 | 1/2006 | O'Rear et al. | |
| 7,091,391 | B2 | 8/2006 | Stauffer | |
| 8,519,210 | B2 | 8/2013 | Arnold et al. | |
| 9,409,156 | B2 | 8/2016 | Sanchez Valente et al. | |
| 2014/0080699 | A1 | 3/2014 | Ghose et al. | |
| 2014/0107385 | A1 | 4/2014 | Schammel et al. | |
| 2015/0151280 | A1 | 6/2015 | Sanchez Valente et al. | |
| 2017/0226030 | A1 * | 8/2017 | Li | C10G 9/36 |

FOREIGN PATENT DOCUMENTS

| | | |
|---|---|---|
| EP | 0316075 A1 | 5/1989 |
| EP | 0205117 B1 | 9/1989 |
| EP | 0179131 B1 | 1/1990 |
| EP | 0206043 B1 | 3/1990 |
| WO | 8504866 A1 | 11/1985 |
| WO | 2016049144 A1 | 3/2016 |
| WO | 2018148141 A1 | 8/2018 |
| WO | 2018148145 A1 | 8/2018 |

OTHER PUBLICATIONS

Gärtner, Christian A., et al., "Oxidative Dehydrogenation of Ethane: Common Principles and Mechanistic Aspects," ChemCatChem, 2013, vol. 5, Issue 11, pp. 3196-3217.
Fengchi Yu et al., "Oxidative dehydrogenation of ethane to ethylene in the presence of HCl over CeO2-based catalysts," Chinese Journal of Catalysis, 2014, vol. 35, Issue 8, pp. 1260-1266.
Foreign communication from a related application—International Search Report and Written Opinion of the International Searching Authority, International Application No. PCT/US2018/016855, dated May 23, 2018, 11 pages.
Burch, R., et al., "The Importance of Heterogeneous and Homogeneous Reactions in Oxidative Coupling of Methane Over Chloride Promoted Oxide Catalysts," Catalysis Letters, 1989, pp. 249-256, vol. 2, J.C. Baltzer A.G. Scientific Publishing Company.
Burch, R., et al., "Role of Chlorine in Improving Selectivity in the Oxidative Coupling of Methane to Ethylene," Applied Catalysis, 1989, pp. 69-87, vol. 46, Elsevier Science Publishers B.V.
Djamalova, S.A., et al., Nephtekimiya, 1989, pp. 780-785, vol. 29, No. 6.
Filing Receipt and Specification of U.S. Appl. No. 16/483,689 entitled, "A Process for Catalytic Oxidative Conversion of Methane to Ethylene in the Presence of Chlorine Intermediates," filed Aug. 5, 2019, 38 pages.
Filing Receipt and Specification of U.S. Appl. No. 62/455,749, entitled, "A Process for Catalytic Oxidative Dehydrogenation of Ethane to Ethylene in the Presence of Chlorine Intermediates," filed Feb. 7, 2017, 35 pages.

(Continued)

Primary Examiner — Philip Y Louie
(74) Attorney, Agent, or Firm — Conley Rose, P.C.; Rodney P. Carroll

(57) ABSTRACT

A process for producing ethylene comprising: (a) reacting a reactant mixture in a reactor to yield a product mixture, wherein the reactor comprises a catalyst, wherein the reactant mixture comprises ethane, oxygen, and a chlorine intermediate precursor, wherein the product mixture comprises ethylene, unreacted ethane, carbon monoxide, and carbon dioxide, wherein the catalyst comprises a redox agent, an alkali metal, and a rare earth element; and (b) recovering at least a portion of the ethylene from the product mixture. The reacting in step (a) further comprises (i) contacting at least a portion of the chlorine intermediate precursor with the catalyst to form a chlorinated catalyst; (ii) allowing at least a portion of the chlorinated catalyst to generate a chlorine intermediate; and (iii) allowing at least a portion of the reactant mixture to react via the chlorine intermediate.

20 Claims, No Drawings

(56) References Cited

OTHER PUBLICATIONS

Filing Receipt and Specification of U.S. Appl. No. 62/455,766, entitled, "A Process for Catalytic Oxidative Conversion of Methane to Ethylene in the Presence of Chlorine Intermediates," filed Feb. 7, 2017, 41 pages.

Foreign communication from a related application—International Preliminary Report on Patentability, International Application No. PCT/US2018/016833, dated Aug. 22, 2019, 10 pages.

Foreign communication from a related application—International Preliminary Report on Patentability, International Application No. PCT/US2018/016855, dated Aug. 22, 2019, 8 pages.

Foreign communication from a related application—International Search Report and Written Opinion of the International Searching Authority of International Application No. PCT/US2018/016833, dated May 15, 2018, 14 pages.

Korf, S.J., et al., "Effect of Additives on Lithium Doped Magnesium Oxide Catalysts Used in the Oxidative Coupling of Methane," Applied Catalysis, 1989, pp. 119-135, vol. 56, Elsevier Science Publishers, B.V.

Lunsford, J.H., "The catalytic conversion of methane to higher hydrocarbons," Catalysis Today, 1990, pp. 235-259, vol. 6, No. 3, Elsevier Science Publishers, B.V.

Lunsford, Jack H., et al., "The Effect of Chloride Ions on a Li+—MgO Catalyst for the Oxidative Coupling of Methane," Journal of Catalysis, 1994, pp. 301-310, vol. 147, Academic Press, Inc.

Mamedov, A. Kh., et al., Nephtechimiya, 1988, pp. 786-790, vol. 28, No. 6.

Mamedov, A. Kh., et al., "Intermediate Oxygen-Containing Compounds in Oxidative Condensation of Methane Over Sodium-Manganese Catalysts," React. Kinet. Catal. Lett., 1991, pp. 283-289, vol. 45, No. 2.

Roos, J.A., et al., "Selective oxidation of methane to ethane and ethylene over various oxide catalysts," Catalysis Today, 1987, pp. 133-145, vol. 1, Elsevier Science Publishers, B.V.

Shischak, E.V., et al. "Effect of HCl Partial Pressure on the Oxidative Coupling of Methane," React. Kinet. Catal. Lett., 1998, pp. 41-45, vol. 65, No. 1, Elsevier Science, B.V. and Akadémiai Kiadó.

Swaan, H.M., et al., "The oxidative coupling of methane and the oxidative dehydrogenation of ethane over a niobium promoted lithium doped magnesium oxide catalyst," Catalysis Today, 1993, pp. 537-546, vol. 16, Elsevier Science Publishers B.V.

* cited by examiner

PROCESS FOR CATALYTIC OXIDATIVE DEHYDROGENATION OF ETHANE TO ETHYLENE IN THE PRESENCE OF CHLORINE INTERMEDIATES

CROSS REFERENCE TO RELATED APPLICATIONS

This application is a continuation of and claims priority to International Application No. PCT/US2018/016855 filed Feb. 5, 2018 and entitled "A Process for Catalytic Oxidative Dehydrogenation of Ethane to Ethylene in the Presence of Chlorine Intermediates," which claims priority to U.S. Provisional Application No. 62/455,749 field Feb. 7, 2017, which applications are incorporated by reference herein in their entirety.

TECHNICAL FIELD

The present disclosure relates to methods of producing hydrocarbons, more specifically methods of producing olefins, such as ethylene, by oxidative dehydrogenation of ethane in the presence of chlorine radicals.

BACKGROUND

Hydrocarbons, and specifically olefins such as ethylene ($C_2H_4$), are typically building blocks used to produce a wide range of products, for example, break-resistant containers and packaging materials. Currently, for industrial scale applications, ethylene can be produced by steam cracking, or by heating natural gas condensates and petroleum distillates, which include ethane and higher hydrocarbons, and the produced ethylene is separated from a product mixture by using gas separation processes. However, steam cracking uses expensive furnace technology which generally involves the use of metal coils for a reactor converting ethane in a mixture with water vapor to ethylene. Due to the frequent blockage of these metal coils by coke fragments, ethane steam cracking processes require periodic cleaning of the metal coils.

Thus, there is an ongoing need for the development of ethane dehydrogenation processes that can increase the production of ethylene.

BRIEF SUMMARY

Disclosed herein is a process for producing ethylene comprising (a) reacting a reactant mixture in a reactor to yield a product mixture, wherein the reactor comprises a catalyst, wherein the reactant mixture comprises ethane, oxygen, and a chlorine intermediate precursor, wherein the product mixture comprises ethylene, unreacted ethane, carbon monoxide, and carbon dioxide, wherein the catalyst comprises a redox agent, an alkali metal, and a rare earth element, and (b) recovering at least a portion of the ethylene from the product mixture.

Also disclosed herein is a process for producing ethylene comprising (a) reacting a reactant mixture in a reactor to yield a product mixture, wherein the reactor comprises a catalyst, wherein the reactant mixture comprises ethane, oxygen, and a chlorine radical precursor, wherein the product mixture comprises ethylene, unreacted ethane, carbon monoxide, and carbon dioxide, wherein the catalyst comprises a redox agent, an alkali metal, and lanthanum (La), and (b) recovering at least a portion of the ethylene from the product mixture.

DETAILED DESCRIPTION

Disclosed herein are processes for producing ethylene comprising (a) reacting a reactant mixture in a reactor at a temperature of less than about 750° C. to yield a product mixture, wherein the reactor comprises a catalyst, wherein the reactant mixture comprises ethane, oxygen, and a chlorine intermediate precursor, wherein the product mixture comprises ethylene, unreacted ethane, carbon monoxide, and carbon dioxide, wherein the catalyst comprises a redox agent, an alkali metal, and a rare earth element; and (b) recovering at least a portion of the ethylene from the product mixture. In some aspects, the redox agent comprises manganese (Mn), the alkali metal comprises sodium (Na), and the rare earth element comprises lanthanum (La).

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

In an aspect, a process for producing ethylene as disclosed herein can comprise reacting a reactant mixture in a reactor to yield a product mixture, wherein the reactor comprises a catalyst, wherein the reactant mixture comprises ethane ($C_2H_6$), oxygen ($O_2$), and a chlorine intermediate precursor, wherein the product mixture comprises ethylene ($C_2H_4$), unreacted ethane, carbon monoxide, and carbon dioxide, and wherein the catalyst comprises a redox agent, an alkali metal, and a rare earth element. As will be appreciated by one of skill in the art, and with the help of this disclosure, the reactant mixture may comprise one or more reactive components (e.g., one or more hydrocarbons, such as $C_2H_6$; $O_2$) and one or more inert components (e.g., a diluent, such as nitrogen, water, etc.), and the one or more reactive components of the reactant mixture may react in order to form one or more reaction products (e.g., $C_2H_4$, carbon monoxide (CO), carbon dioxide ($CO_2$), etc.).

In an aspect, the reactor can comprise an adiabatic reactor, an autothermal reactor, a tubular reactor, a continuous flow reactor, and the like, or combinations thereof.

In an aspect, the reactor can be characterized by a pressure (e.g., reactor pressure, reaction pressure) of from about ambient pressure (e.g., atmospheric pressure) to about 500 psig, alternatively from about ambient pressure to about 200 psig, or alternatively from about ambient pressure to about 100 psig. In an aspect, the process for producing ethylene as disclosed herein can be carried out at ambient pressure.

In an aspect, the reactor can be characterized by a temperature (e.g., reactor temperature, reaction temperature) of less than about 750° C., alternatively less than about 725° C., alternatively less than about 700° C., alternatively less than about 690° C., alternatively from about 650° C. to about 750° C., alternatively from about 675° C. to about 725° C., alternatively from about 680° C. to about 700° C., or alternatively about 690° C.

In some aspects, the process can be characterized by a temperature (e.g., reactor temperature, reaction temperature) that is decreased when compared to a temperature of an otherwise similar process conducted (1) with a reactant mixture comprising ethane and oxygen without the chlorine intermediate precursor; and/or (2) with a catalyst comprising a redox agent and an alkali metal without the rare earth element.

The reactant mixture can comprise $C_2H_6$ from any suitable source. In an aspect, the $C_2H_6$ suitable for use in the present disclosure as part of the reactant mixture can be $C_2H_6$ separated from natural gas, associated gas, well gas, etc.; $C_2H_6$ produced as a by-product of various chemical processes, such as cracking, hydrocracking, hydroprocessing, etc.; and the like; or combinations thereof.

The $O_2$ used in the reactant mixture can be oxygen gas (which may be obtained via a membrane separation process), technical oxygen (which may contain some air), air, oxygen enriched air, and the like, or combinations thereof.

The reactant mixture can further comprise a diluent. The diluent is inert with respect to the ethane conversion reactions, e.g., the diluent does not participate in the ethane conversion reactions. In an aspect, the diluent can comprise water, steam, nitrogen, inert gases (e.g., argon), and the like, or combinations thereof. In an aspect, the diluent can be present in the reactant mixture in an amount of from about 0.5% to about 80%, alternatively from about 5% to about 50%, or alternatively from about 10% to about 30%, based on the total volume of the reactant mixture. In some aspects, the diluent can be water and/or nitrogen.

In an aspect, the reactant mixture can be characterized by a $C_2H_6/O_2$ molar ratio of from about 2:1 to about 6:1, alternatively from about 2.5:1 to about 3:1, or alternatively from about 3:1 to about 4:1.

The catalyst can comprise a redox agent. Nonlimiting examples of redox agents suitable for use in the catalysts of the present disclosure include manganese (Mn), tin (Sn), bismuth (Bi), cerium (Ce), and the like, or combinations thereof. In an aspect, the redox agent is manganese (Mn).

In an aspect, the catalyst can comprise the redox agent in an amount of from about 1 wt. % to about 25 wt. %, alternatively from about 5 wt. % to about 22.5 wt. %, alternatively from about 10 wt. % to about 20 wt. %, or alternatively from about 12.5 wt. % to about 17.5 wt. %, based on the total weight of the catalyst.

The catalyst can comprise an alkali metal. The alkali metal comprises sodium (Na), potassium (K), rubidium (Rb), cesium (Cs), or combinations thereof. In an aspect, the alkali metal is sodium (Na).

In an aspect, the catalyst comprises an alkali metal in an amount of less than about 20 wt. %, alternatively less than about 15 wt. %, alternatively less than about 12.5 wt. %, alternatively less than about 10 wt. %, alternatively equal to or greater than about 1 wt. %, alternatively equal to or greater than about 3 wt. %, alternatively equal to or greater than about 5 wt. %, alternatively equal to or greater than about 7.5 wt. %, alternatively from about 1 wt. % to about 20 wt. %, alternatively from about 3 wt. % to about 20 wt. %, alternatively from about 5 wt. % to about 15 wt. %, or alternatively from about 7.5 wt. % to about 12.5 wt. %, based on the total weight of the catalyst.

The catalyst can comprise a rare earth element. Nonlimiting examples of rare earth elements suitable for use in the catalysts of the present disclosure include lanthanum (La), cerium (Ce), praseodymium (Pr), neodymium (Nd), samarium (Sm), dysprosium (Dy), gadolinium (Gd), yttrium (Y), scandium (Sc), and the like, or combinations thereof. In an aspect, the catalyst can comprise any suitable rare earth element that can form an oxychloride (e.g., an oxychloride of an rare earth element). In an aspect, the rare earth element is lanthanum (La).

In an aspect, the catalyst can comprise the rare earth element in an amount of from about 0.5 wt. % to about 10 wt. %, alternatively from about 1 wt. % to about 7.5 wt. %, alternatively from about 1 wt. % to about 5 wt. %, or alternatively from about 2.5 wt. % to about 5 wt. %, based on the total weight of the catalyst.

In an aspect, the catalyst can comprise one or more oxides of the redox agent; one or more oxides of the alkali metal; one or more oxides of the rare earth element; and the like; or combinations thereof. Nonlimiting examples of oxides suitable for use in the catalysts of the present disclosure include $Na_2O$, $Cs_2O$, $Mn_3O_4$, $MnO$, $SnO_2$, $La_2O_3$, $Ce_2O_3$, $Sm_2O_3$, $La_2O_3$—$CeO_2$—$Na_2O$, $Na_2O$—$MnO$—$La_2O_3$, and the like, or combinations thereof.

In an aspect, the catalysts suitable for use in the present disclosure can be supported catalysts and/or unsupported catalysts.

In an aspect, the catalysts suitable for use in the present disclosure can further comprises a support, wherein at least a portion of the catalyst contacts, coats, is embedded in, is supported by, and/or is distributed throughout at least a portion of the support.

In an aspect, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), calcium oxide (CaO), strontium oxide (SrO), zirconium oxide ($ZrO_2$), zinc oxide (ZnO), lithium aluminum oxide ($LiAlO_2$), magnesium aluminum oxide ($MgAlO_4$), manganese oxides (MnO, $MnO_2$, $Mn_3O_4$), lanthanum oxide ($La_2O_3$), activated carbon, silica gel, zeolites, activated clays, silicon carbide (SiC), diatomaceous earth, magnesia, aluminosilicates, calcium aluminate, carbonates, $MgCO_3$, $CaCO_3$, $SrCO_3$, $BaCO_3$, $Y_2(CO_3)_3$, $La_2(CO_3)_3$, and the like, or combinations thereof. In some aspects, the support can comprise MgO, $Al_2O_3$, $SiO_2$, $ZrO_2$, and the like, or combinations thereof.

In some aspects, the supported catalysts can comprise a support, wherein the support can be inert or catalytically inactive (e.g., the support cannot catalyze a $C_2H_6$ conversion reaction to $C_2H_4$), such as $SiO_2$. In such aspects, the catalyst can comprise Na—MnO—$La_2O_3$/$SiO_2$.

In other aspects, the supported catalysts can comprise a support, wherein the support can be catalytically active (e.g., the support can catalyze a $C_2H_6$ conversion reaction to $C_2H_4$). For example, the catalytically active support can comprise a metal oxide support, such as MgO and/or $Al_2O_3$. In an aspect, the catalyst can further exclude an inert support, wherein the catalyst can comprise Na—MnO—$WO_3$—$La_2O_3$, Na—MnO—$La_2O_3$/$Al_2O_3$, or both Na—MnO—$WO_3$—$La_2O_3$ and Na—MnO—$La_2O_3$/$Al_2O_3$. Without wishing to be limited by theory, some types of alumina can be considered inert supports, such as alpha alumina; while other types of alumina can be considered active supports, such as gamma alumina. As will be appreciated by one of skill in the art, and with the help of this disclosure, different types of alumina, such as alpha alumina, beta alumina, gamma alumina, etc. could be used as a support in the present disclosure, and based on the type or types of alumina used, the support could be either active or inactive/inert. In aspects where a more inert alumina support is desired, alpha alumina can be used. In aspects where a more active alumina support is desired, gamma alumina can be used. Further, as will be appreciated by one of skill in the art, and with the help of this disclosure, gamma alumina is more acidic (by comparison with alpha alumina, for example), and as such alpha alumina can be used instead where inert alumina supports are preferred.

In yet other aspects, the supported catalysts can comprise a catalytically active support and a catalytically inactive support.

In an aspect, yielding the product mixture can comprise allowing a first portion of the reactant mixture to react via an oxidative conversion reaction, in the presence of the catalyst, as represented by equation (1):

$$C_2H_6 + \tfrac{1}{2}O_2 \rightarrow C_2H_4 + H_2O \quad (1)$$

Oxidative conversion of ethane to ethylene is exothermic. Excess heat produced from the oxidative conversion of ethane (equation (1)) can push conversion of ethane to carbon monoxide and carbon dioxide rather than the desired $C_2$ hydrocarbon product (e.g., ethylene), via deep oxidation reactions, as represented by equations (2) and (3):

$$C_2H_6 + 2.5O_2 \rightarrow 2CO + 3H_2O \quad (2)$$

$$C_2H_6 + 3.5O_2 \rightarrow 2CO_2 + 3H_2O \quad (3)$$

In some aspects, the chlorine intermediate precursor can be introduced to the reactor as part of the reactant mixture, e.g., the chlorine intermediate precursor can be added to the reactant mixture (e.g., ethane and oxygen) and can be introduced to the reactor with the ethane and oxygen via a common stream. In other aspects, the chlorine intermediate precursor can be introduced to the reactor via a stream other than the feed stream for ethane and oxygen (e.g., separate stream).

In an aspect, yielding the product mixture can further comprise (i) allowing at least a portion of the chlorine intermediate precursor to generate a chlorine intermediate, and (ii) allowing a second portion of the reactant mixture to react via the chlorine intermediate.

In an aspect, the chlorine intermediate precursor can be a chlorine radical precursor, wherein the chlorine intermediate is a chlorine radical. The chlorine intermediate precursor can comprise hydrogen chloride (HCl), methyl chloride ($CH_3Cl$), methylene chloride ($CH_2Cl_2$), chloroform ($CHCl_3$), carbon tetrachloride ($CCl_4$), ethyl chloride ($C_2H_5Cl$), 1,2-dichloroethane ($C_2H_4Cl_2$), trichloroethylene ($C_2HCl_3$), and the like, or combinations thereof.

The stoichiometric reactions of ethane conversion with the introduction of a chlorine intermediate precursor to the reactor can be described similar to the case of oxidative conversion of ethane reaction, as represented by equations (4)-(8) for various chlorine intermediate precursors:

$$C_2H_6 + \tfrac{1}{2}O_2 + (HCl) \rightarrow C_2H_4 + H_2O \quad (4)$$

$$C_2H_6 + \tfrac{1}{2}O_2 + (CH_3Cl) \rightarrow C_2H_4 + H_2O \quad (5)$$

$$C_2H_6 + \tfrac{1}{2}O_2 + (CH_2Cl_2) \rightarrow C_2H_4 + H_2O \quad (6)$$

$$C_2H_6 + \tfrac{1}{2}O_2 + (CCl_4) \rightarrow C_2H_4 + H_2O \quad (7)$$

$$C_2H_6 + \tfrac{1}{2}O_2 + (C_2H_5Cl) \rightarrow C_2H_4 + H_2O \quad (8)$$

Without wishing to be limited by theory, the chlorine intermediate precursors do not get consumed in reactions (4)-(8), due to a radical mechanism of chlorine participation in the reactions that can regenerate the chlorine intermediate precursors.

The chlorine intermediate precursor can be introduced to the reactor in an amount of from about 0.5 vol. % to about 5 vol. %, alternatively from about 0.5 vol. % to about 3 vol. %, alternatively from about 0.75 vol. % to about 3 vol. %, alternatively from about 1 vol. % to about 3 vol. %, alternatively from about 0.75 vol. % to about 4 vol. %, alternatively from about 1 vol. % to about 5 vol. %, alternatively from about 2 vol. % to about 5 vol. %, alternatively from about 2.5 vol. % to about 4.5 vol. %, alternatively from about 3 vol. % to about 4 vol. %, or alternatively about 3 vol. %, based on the total volume of the reactant mixture.

In an aspect, the chlorine intermediate precursor can generate a chlorine intermediate via contacting at least a portion of the chlorine intermediate precursor with the catalyst to form a chlorinated catalyst, wherein at least a portion of the chlorinated catalyst can generate the chlorine intermediate. Without wishing to be limited by theory, the alkali metal of the catalyst reacts with the chlorine intermediate precursor that was introduced in a gas phase (e.g., with the reactant mixture) to the reactor and forms chlorides on a catalyst surface. As will be appreciated by one of skill in the art, and with the help of this disclosure, the more alkali metal in the catalyst, the more chlorides will be formed on the catalyst surface (e.g., the larger the chlorides surface coverage on the catalyst surface). For purposes of the disclosure herein, the term "chlorine intermediate precursor" refers to both a chlorine compound introduced in gas phase to the reactor, as well as a chloride, oxychloride or any other chlorine-containing compound adsorbed and/or formed on a surface of the catalyst (e.g., chlorinated catalyst), wherein such chloride, oxychloride or any other chlorine-containing compound adsorbed and/or formed on a surface of the catalyst can further generate a chlorine intermediate, such as a chlorine radical. For purposes of the disclosure herein, the term "chlorinated catalyst" refers to a catalyst having a chloride, oxychloride or any other chlorine-containing compound adsorbed and/or formed on a surface of the catalyst, wherein such chloride, oxychloride or any other chlorine-containing compound adsorbed and/or formed on a surface of the catalyst (e.g., chlorinated catalyst) can further generate a chlorine intermediate, such as a chlorine radical.

The chlorinated catalyst can comprise an oxychloride of a rare earth element, such as lanthanum oxychloride (LaOCl), cerium oxychloride, praseodymium oxychloride, neodymium oxychloride, samarium oxychloride, dysprosium oxychloride, gadolinium oxychloride, yttrium oxychloride, scandium oxychloride, and the like, or combinations thereof. In an aspect, the chlorinated catalyst can comprise LaOCl. As will be appreciated by one of skill in the art, and with the help of this disclosure, the more rare earth elements in the catalyst, the more rare earth element oxychlorides will be formed on the catalyst surface (e.g., the larger the oxychlorides surface coverage on the catalyst surface).

In an aspect, the chlorinated catalyst can generate an amount of chlorine radicals that is increased when compared to an amount of chlorine radicals generated by an otherwise similar chlorinated catalyst comprising a redox agent and an alkali metal without the rare earth element (e.g., La). As will be appreciated by one of skill in the art, and with the help of this disclosure, the chlorinated catalysts comprise rare earth element oxychlorides that promote the formation of chlorine radicals.

Without wishing to be limited by theory, the chloride, oxychloride or any other chlorine-containing compound adsorbed and/or formed on the catalyst surface (e.g., chlorinated catalyst) can further generate the chlorine intermediate (e.g., chlorine radical), for example via a redox agent, such as Mn. Redox agents can generally convert between oxide forms and chloride forms, which can lead to the formation of chlorine intermediates, thus promoting ethane conversion reactions via chlorine intermediates. Further, and without wishing to be limited by theory, the chloride, oxychloride or any other chlorine-containing compound adsorbed and/or formed on the catalyst surface can react with oxygen centers on the chlorinated catalyst (e.g., on the catalyst surface) to generate the chlorine intermediate (e.g., chlorine radical), for example by reducing such oxygen centers on the catalyst while oxidizing a chloride and/or oxychloride to a chlorine radical. Further, and without wishing to be limited by theory, chlorides, oxychlorides or any other chlorine-containing compound adsorbed and/or formed on the chlorinated catalyst surface can decrease the amount of oxygen available for deep oxidation reactions (e.g., by reducing oxygen centers), thereby minimizing deep oxidation reactions, for example deep oxidation reactions of ethane to carbon dioxide.

For example, when the catalyst comprises Mn, such as in the form of manganese oxides (e.g., $MnO_2$), and when the chlorine intermediate precursor comprises HCl, the generation of chlorine radicals (Cl.) can be represented by equations (9) and (10):

$$MnO_2 + 4HCl \rightleftharpoons MnCl_2 + Cl_2 + 2H_2O \quad (9)$$

$$Cl_2 \rightleftharpoons 2Cl. \quad (10)$$

Without wishing to be limited by theory, the chlorine intermediate (e.g., chlorine radical, Cl.) can diffuse away from the catalyst surface (e.g., into the gas phase) and can initiate the formation of ethyl radicals, and ultimately the formation of ethylene molecules. The chlorine intermediate (e.g., chlorine radical, Cl.) can re-generate the HCl while forming various alkyl radicals (e.g., ethyl radicals ($C_2H_5$.)), and such HCl can re-initiate the steps of forming the chlorine radical by interacting with the catalyst (e.g., for example according to reactions (9) and (10)); and/or in gas phase, for example as represented by equations (11) and (12):

$$C_2H_6 + Cl. \rightleftharpoons C_2H_5. + HCl \quad (11)$$

$$C_2H_5. \rightleftharpoons C_2H_4 + H. \quad (12)$$

As will be appreciated by one of skill in the art, and with the help of this disclosure, methane ($CH_4$) and methyl radicals ($CH_3$.) can also be formed during the propagation of ethane oxidative conversion reactions in the absence of the chlorine intermediate precursors, as well as during the propagation of ethane oxidative conversion reactions in the presence of the chlorine intermediate precursors.

As disclosed herein, in the presence of chlorine intermediate precursors, (A) the oxidative conversion reactions (e.g., a first portion of the reactant mixture reacting via an ethane oxidative conversion reaction, for example as represented by equation (1)) and (B) reactions via a chlorine intermediate (e.g., a second portion of the reactant mixture reacting via the chlorine intermediate, for example as represented by equations (11) and (12)) can occur simultaneously.

In an aspect, a process for producing ethylene as disclosed herein can comprise recovering at least a portion of the product mixture from the reactor, wherein the product mixture can be collected as an outlet gas mixture from the reactor.

In an aspect, the product mixture can be characterized by an ethylene to ethane molar ratio that is increased when compared to an ethylene to ethane molar ratio of a product mixture produced via an otherwise similar process conducted (1) with a reactant mixture comprising ethane and oxygen without the chlorine intermediate precursor; and/or (2) with a catalyst comprising a redox agent and an alkali metal without the rare earth element.

In an aspect, the product mixture can be characterized by an ethylene to ethane molar ratio of equal to or greater than about 0.2:1, alternatively equal to or greater than about 0.5:1, alternatively equal to or greater than about 1:1, alternatively equal to or greater than about 5:1, alternatively equal to or greater than about 10:1, alternatively from about 0.2:1 to about 10:1, alternatively from about 1:1 to about 10:1, or alternatively from about 5:1 to about 9:1.

In an aspect, the product mixture can comprises less than about 10 mol %, alternatively less than about 7.5 mol %, or alternatively less than about 5 mol % carbon dioxide ($CO_2$). The process for producing ethylene as disclosed herein can comprise minimizing deep oxidation of ethane to $CO_2$.

In an aspect, the product mixture can be characterized by a carbon monoxide to carbon dioxide molar ratio that is increased when compared to a carbon monoxide to carbon dioxide molar ratio of a product mixture produced via an otherwise similar process conducted (1) with a reactant mixture comprising ethane and oxygen without the chlorine intermediate precursor; and/or (2) with a catalyst comprising a redox agent and an alkali metal without the rare earth element.

In an aspect, the product mixture can be characterized by a carbon monoxide to carbon dioxide molar ratio of equal to or greater than about 0.4:1, alternatively equal to or greater than about 1:1, or alternatively equal to or greater than about 2:1.

In an aspect, a process for producing ethylene as disclosed herein can comprise recovering at least a portion of the ethylene from the product mixture. The product mixture can comprise ethylene, unreacted ethane, and optionally a diluent. The water produced from the ethane conversion reaction and the water used as a diluent (if water diluent is used) can be separated from the product mixture prior to separating any of the other product mixture components. For example, by cooling down the product mixture to a temperature where the water condenses (e.g., below 100° C. at ambient pressure), the water can be removed from the product mixture, by using a flash chamber for example.

In an aspect, at least a portion of ethylene can be separated from the product mixture to yield recovered ethylene and recovered hydrocarbons, by using any suitable separation technique (e.g., distillation, cryogenic distillation). In some aspects, at least a portion of the recovered hydrocarbons (e.g., recovered hydrocarbons after olefin separation, such as separation of $C_2H_4$ and $C_3H_6$) can be converted to ethylene, for example via a conventional steam cracking process.

In an aspect, at least a portion of the unreacted ethane can be separated from the product mixture to yield recovered ethane. Ethane can be separated from the product mixture by using any suitable separation technique, such as for example distillation (e.g., cryogenic distillation). At least a portion of the recovered ethane can be recycled to the reactant mixture. In some aspects, the recovered ethane can comprise at least a portion of the methane produced as a by-product of the ethane oxidative conversion reactions.

In some aspects, at least a portion of the carbon monoxide can be separated from the product mixture to yield recovered carbon monoxide. The recovered carbon monoxide can be used in syngas, and the syngas can be further used for a variety of processes, such as methanol production processes.

In an aspect, a process for producing ethylene can comprise (a) reacting a reactant mixture in a reactor to yield a product mixture, wherein the reactor comprises a catalyst, wherein the reactor is characterized by a reaction temperature of less than about 700° C., or alternatively less than about 690° C., wherein the reactant mixture comprises ethane, oxygen, and HCl, wherein the HCl is present in the reactant mixture in an amount of from about 1 vol. % to about 3 vol. %, based on the total volume of the reactant mixture, wherein the product mixture comprises ethylene, unreacted ethane, carbon monoxide, and carbon dioxide, wherein the catalyst comprises (1) manganese (Mn) in an amount of from about 10 wt. % to about 20 wt. %, based on the total weight of the catalyst, (2) sodium (Na) in an amount of from about 5 wt. % to about 15 wt. %, based on the total weight of the catalyst, (3) lanthanum (La) in an amount of from about 1 wt. % to about 5 wt. %, based on the total weight of the catalyst, and (4) a $SiO_2$ support; and (b) recovering at least a portion of the ethylene from the product mixture. The step (a) of reacting further comprises (i) contacting at least a portion of the HCl with the catalyst to form a chlorinated catalyst, wherein the chlorinated catalyst comprises lanthanum oxychloride (LaOCl); (ii) allowing at least a portion of the chlorinated catalyst to generate a chlorine radical; and (iii) allowing at least a portion of the reactant mixture to react via the chlorine radical. In such aspect, the product mixture can be characterized by an ethylene to ethane molar ratio of equal to or greater than about 10:1.

In an aspect, a process for producing ethylene as disclosed herein can advantageously display improvements in one or more process characteristics when compared to an otherwise similar process conducted with a catalyst that has not been activated via a chlorine intermediate precursor. The process for producing ethylene as disclosed herein can advantageously minimize deep oxidation reactions to $CO_2$. In an aspect, a process for producing ethylene as disclosed herein can advantageously be characterized by an amount of carbon dioxide in the product mixture that is decreased when compared to an amount of carbon dioxide in a product mixture produced via an otherwise similar process conducted (1) with a reactant mixture comprising ethane and oxygen without the chlorine intermediate precursor; and/or (2) with a catalyst comprising a redox agent and an alkali metal without the rare earth element.

In an aspect, a process for producing ethylene as disclosed herein can advantageously be characterized by an ethane conversion that is increased when compared to an ethane conversion of an otherwise similar process conducted (1) with a reactant mixture comprising ethane and oxygen without the chlorine intermediate precursor, and/or (2) with a catalyst comprising a redox agent and an alkali metal without the rare earth element.

In an aspect, a process for producing ethylene as disclosed herein can advantageously be characterized by an ethylene selectivity that is increased when compared to an ethylene selectivity of an otherwise similar process conducted (1) with a reactant mixture comprising ethane and oxygen without the chlorine intermediate precursor, and/or (2) with a catalyst comprising a redox agent and an alkali metal without the rare earth element. Generally, a selectivity to a desired product or products (e.g., ethylene selectivity) refers to how much desired product (e.g., ethylene) was formed divided by the total products formed, both desired and undesired (e.g., ethylene, carbon dioxide, etc.). For purposes of the disclosure herein, the selectivity to a desired product is a % selectivity based on moles converted into the desired product. Additional advantages of the processes for the production of ethylene as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

A catalyst composition was prepared as follows. 10 g of dried silica-gel (particle size of 20-50 mesh; drying procedure: 120° C., 2 hours) was impregnated with $Mn(NO_3)_2 \cdot 4H_2O$; $Na_2CO_3 \cdot 2H_2O$; and $La_3(NO_3)_3$ to get a catalyst composition comprising 10% Na-15% Mn-3% La—O/$SiO_2$. A solution of 6.8 g $Mn(NO_3)_2 \cdot 4H_2O$, 3.03 g $Na_2CO_3 \cdot 2H_2O$, and 0.7 g $La_3(NO_3)_3$ in water was added to 10 g $SiO_2$ and heated at 45° C. with continuous stirring. After impregnation, the resulting solid catalyst material was oven dried in air atmosphere for 12 hours at 120° C., and then was calcined for 4 hours in air atmosphere at 850° C. The dried and calcined catalyst was loaded into the reactor and used in the following examples.

Example 2

Oxidative conversion reactions of ethane to ethylene were conducted as follows. The reactant mixture comprised 30 mol % ethane and 70 mol % air. The used catalyst was 10% Na-15% Mn-3% La—O/SiO$_2$, prepared by using the procedure described in Example 1; and the reaction temperature was 690° C. The reactor was a quartz fixed bed reactor with a diameter of 10 mm and a length of 20 cm heated by electrical heating, with a catalyst loading of 7 ml. The reactions were conducted at a gas hourly space velocity (GHSV) of 8,000 h$^{-1}$.

The C$_2$H$_6$ conversion was 54.0%. For example, the ethane conversion can be calculated by using the following equation:

$$C_2H_6 \text{ conversion} = \frac{C^{in}_{C_2H_6} - C^{out}_{C_2H_6}}{C^{in}_{C_2H_6}} \times 100\%$$

wherein $C^{in}_{C_2H_6}$=number of moles of C from C$_2$H$_6$ that entered the reactor as part of the reactant mixture; and $C^{out}_{C_2H_6}$=number of moles of C from C$_2$H$_6$ that was recovered from the reactor as part of the product mixture.

The C$_2$H$_4$ selectivity was 62.0%; the CO selectivity was 5.5%; the CO$_2$ selectivity was 24.5%; and the CH$_4$ selectivity was 8.0%.

Example 3

Oxidative conversion reactions of ethane to ethylene were conducted as described in Example 2, except for the reactant mixture comprising 30 mol % ethane and 70 mol % air, to which 1 mol % HCl was added.

The C$_2$H$_6$ conversion was 92.0%. The C$_2$H$_4$ selectivity was 84.3%; the CO selectivity was 7.2%; the CO$_2$ selectivity was 3.5%; and the CH$_4$ selectivity was 5.0%. By introducing a chlorine radical precursor such as HCl to the reactant mixture, a dramatic increase in both C$_2$H$_6$ conversion and C$_2$H$_4$ selectivity was observed, along with an increase in CO selectivity. Further the CO$_2$ selectivity decreased drastically, along with a decrease in CH$_4$ selectivity. As it can be seen from the data in Examples 2 and 3, the effect of chlorine addition is significant, wherein ethane conversion and ethylene selectivity increase significantly.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

A first aspect, which is a process for producing ethylene comprising (a) reacting a reactant mixture in a reactor to yield a product mixture, wherein the reactor comprises a catalyst, wherein the reactant mixture comprises ethane, oxygen, and a chlorine intermediate precursor, wherein the product mixture comprises ethylene, unreacted ethane, carbon monoxide, and carbon dioxide, wherein the catalyst comprises a redox agent, an alkali metal, and a rare earth element; and (b) recovering at least a portion of the ethylene from the product mixture.

A second aspect, which is the process of the first aspect, wherein the reacting in step (a) further comprises (i) contacting at least a portion of the chlorine intermediate precursor with the catalyst to form a chlorinated catalyst; (ii) allowing at least a portion of the chlorinated catalyst to generate a chlorine intermediate; and (iii) allowing at least a portion of the reactant mixture to react via the chlorine intermediate.

A third aspect, which is the process of the second aspect, wherein the chlorine intermediate precursor is a chlorine radical precursor, and wherein chlorine intermediate is a chlorine radical.

A fourth aspect, which is the process of any one of the first through the third aspects, wherein the chlorinated catalyst comprises an oxychloride of a rare earth element.

A fifth aspect, which is the process of the fourth aspect, wherein the oxychloride comprises lanthanum oxychloride (LaOCl).

A sixth aspect, which is the process of any one of the first through the fifth aspects, wherein the chlorine intermediate precursor is present in the reactant mixture in an amount of from about 0.5 vol. % to about 5 vol. %, based on the total volume of the reactant mixture.

A seventh aspect, which is the process of any one of the first through the sixth aspects, wherein the chlorine intermediate precursor comprises hydrogen chloride, methyl chloride, methylene chloride, chloroform, carbon tertrachloride, ethyl chloride, 1,2-dichloroethane, trichloroethylene, or combinations thereof.

An eighth aspect, which is the process of any one of the first through the seventh aspects, wherein the redox agent is present in the catalyst in an amount of from about 1 wt. % to about 25 wt. %, based on the total weight of the catalyst.

A ninth aspect, which is the process of any one of the first through the eighth aspects, wherein the redox agent comprises manganese (Mn), tin (Sn), bismuth (Bi), cerium (Ce), or combinations thereof.

A tenth aspect, which is the process of any one of the first through the ninth aspects, wherein the redox agent is manganese (Mn).

An eleventh aspect, which is the process of any one of the first through the tenth aspects, wherein the alkali metal is present in the catalyst in an amount of from about 1 wt. % to about 20 wt. %, based on the total weight of the catalyst.

A twelfth aspect, which is the process of any one of the first through the eleventh aspects, wherein the alkali metal comprises sodium (Na), potassium (K), rubidium (Rb), cesium (Cs), or combinations thereof.

A thirteenth aspect, which is the process of any one of the first through the twelfth aspects, wherein the alkali metal is sodium (Na).

A fourteenth aspect, which is the process of any one of the first through the thirteenth aspects, wherein the rare earth element is present in the catalyst in an amount of from about 0.5 wt. % to about 10 wt. %, based on the total weight of the catalyst.

A fifteenth aspect, which is the process of any one of the first through the fourteenth aspects, wherein the rare earth element comprises lanthanum (La), cerium (Ce), praseodymium (Pr), neodymium (Nd), samarium (Sm), dysprosium (Dy), gadolinium (Gd), yttrium (Y), scandium (Sc), or combinations thereof.

A sixteenth aspect, which is the process of any one of the first through the fifteenth aspects, wherein the rare earth element is lanthanum (La).

A seventeenth aspect, which is the process of any one of the first through the sixteenth aspects, wherein the catalyst comprises one or more oxides of the redox agent; one or more oxides of the alkali metal; one or more oxides of the rare earth element; or combinations thereof.

An eighteenth aspect, which is the process of the seventeenth aspect, wherein the catalyst further excludes an inert support.

A nineteenth aspect, which is the process of the eighteenth aspect, wherein the catalyst comprises Na—MnO—WO$_3$—La$_2$O$_3$, Na—MnO—La$_2$O$_3$/Al$_2$O$_3$, or both Na—MnO—WO$_3$—La$_2$O$_3$ and Na—MnO—La$_2$O$_3$/Al$_2$O$_3$.

A twentieth aspect, which is the process of any one of the first through the seventeenth aspects, wherein the catalyst further comprises an inert support.

A twenty-first aspect, which is the process of the twentieth aspect, wherein the catalyst comprises Na—MnO—La$_2$O$_3$/SiO$_2$.

A twenty-second aspect, which is the process of any one of the first through the seventeenth aspects, wherein the catalyst further comprises a support; wherein at least a portion of the catalyst contacts, coats, is embedded in, is supported by, and/or is distributed throughout at least a portion of the support; and wherein the support comprises MgO, Al$_2$O$_3$, SiO$_2$, ZrO$_2$, or combinations thereof.

A twenty-third aspect, which is the process of any one of the first through the twenty-second aspects, wherein the process is characterized by a temperature that is decreased when compared to a temperature of an otherwise similar process conducted (1) with a reactant mixture comprising ethane and oxygen without the chlorine intermediate precursor, and/or (2) with a catalyst comprising a redox agent and an alkali metal without the rare earth element.

A twenty-fourth aspect, which is the process of any one of the first through the twenty-third aspects, wherein the reacting is characterized by a temperature of less than about 750° C.

A twenty-fifth aspect, which is the process of any one of the first through the twenty-fourth aspects, wherein the reacting is characterized by a temperature of from about 650° C. to about 750° C.

A twenty-sixth aspect, which is the process of any one of the first through the twenty-fifth aspects, wherein the reacting is characterized by a temperature of less than about 700° C.

A twenty-seventh aspect, which is the process of any one of the first through the twenty-sixth aspects, wherein the product mixture is characterized by an ethylene to ethane molar ratio that is increased when compared to an ethylene to ethane molar ratio of a product mixture produced via an otherwise similar process conducted (1) with a reactant mixture comprising ethane and oxygen without the chlorine intermediate precursor, and/or (2) with a catalyst comprising a redox agent and an alkali metal without the rare earth element.

A twenty-eighth aspect, which is the process of any one of the first through the twenty-seventh aspects, wherein the process is characterized by an ethylene selectivity that is increased when compared to an ethylene selectivity of an otherwise similar process conducted (1) with a reactant mixture comprising ethane and oxygen without the chlorine intermediate precursor, and/or (2) with a catalyst comprising a redox agent and an alkali metal without the rare earth element.

A twenty-ninth aspect, which is the process of any one of the first through the twenty-eighth aspects, wherein the process is characterized by an ethane conversion that is increased when compared to an ethane conversion of an otherwise similar process conducted (1) with a reactant mixture comprising ethane and oxygen without the chlorine intermediate precursor, and/or (2) with a catalyst comprising a redox agent and an alkali metal without the rare earth element.

A thirtieth aspect, which is the process of any one of the first through the twenty-ninth aspects further comprising minimizing deep oxidation of ethane to carbon dioxide ($CO_2$).

A thirty-first aspect, which is the process of any one of the first through the thirtieth aspects, wherein the product mixture comprises less than about 10 mol % carbon dioxide ($CO_2$).

A thirty-second aspect, which is the process of any one of the first through the thirty-first aspects, wherein the product mixture is characterized by a carbon monoxide to carbon dioxide molar ratio that is increased when compared to a carbon monoxide to carbon dioxide molar ratio of a product mixture produced via an otherwise similar process conducted (1) with a reactant mixture comprising ethane and oxygen without the chlorine intermediate precursor, and/or (2) with a catalyst comprising a redox agent and an alkali metal without the rare earth element.

A thirty-third aspect, which is the process of any one of the first through the thirty-second aspects, wherein the chlorine intermediate precursor comprises hydrogen chloride (HCl), wherein the redox agent comprises manganese (Mn), wherein the alkali metal comprises sodium (Na), and wherein the rare earth element comprises lanthanum (La).

A thirty-fourth aspect, which is a process for producing ethylene comprising (a) reacting a reactant mixture in a reactor to yield a product mixture, wherein the reactor comprises a catalyst, wherein the reactant mixture comprises ethane, oxygen, and a chlorine radical precursor, wherein the product mixture comprises ethylene, unreacted ethane, carbon monoxide, and carbon dioxide, wherein the catalyst comprises a redox agent, an alkali metal, and lanthanum (La); and (b) recovering at least a portion of the ethylene from the product mixture.

A thirty-fifth aspect, which is the process of the thirty-fourth aspect, wherein the reacting in step (a) further comprises (i) contacting at least a portion of the chlorine radical precursor with the catalyst to form a chlorinated catalyst, wherein the chlorinated catalyst comprises lanthanum oxychloride (LaOCl); (ii) allowing at least a portion of the chlorinated catalyst to generate a chlorine radical; and (iii) allowing at least a portion of the reactant mixture to react via the chlorine radical.

A thirty-sixth aspect, which is the process of the thirty-fifth aspect, wherein the chlorinated catalyst generates an amount of chlorine radicals that is increased when compared to an amount of chlorine radicals generated by an otherwise similar chlorinated catalyst comprising a redox agent and an alkali metal without the La.

A thirty-seventh aspect, which is the process of any one of the thirty-fourth through the thirty-sixth aspects, wherein the chlorine radical precursor comprises hydrogen chloride (HCl); wherein the redox agent comprises manganese (Mn) in an amount of from about 10 wt. % to about 20 wt. %, based on the total weight of the catalyst; wherein the alkali metal comprises sodium (Na) in an amount of from about 5 wt. % to about 15 wt. %, based on the total weight of the catalyst; and wherein the lanthanum (La) is present in an amount of from about 1 wt. % to about 5 wt. %, based on the total weight of the catalyst.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing ethylene comprising:
   (a) reacting a reactant mixture in a reactor comprising a catalyst to yield a product mixture, wherein:
      i. the reactant mixture comprises ethane, oxygen and a chlorine intermediate precursor comprising hydrogen chloride (HCl),
      ii. the product mixture comprises ethylene, unreacted ethane, carbon monoxide, and carbon dioxide,
      iii. the catalyst comprises a redox agent comprising manganese (Mn), an alkali metal comprising sodium (Na), and a rare earth element comprising lanthanum (La), and
      iv. the reactant mixture is characterized by an ethane to oxygen molar ratio of from about 2:1 to about 6:1; and
   (b) recovering at least a portion of the ethylene from the product mixture.

2. The process of claim 1, wherein the reacting in step (a) further comprises (i) contacting at least a portion of the chlorine intermediate precursor with the catalyst to form a chlorinated catalyst; (ii) allowing at least a portion of the chlorinated catalyst to generate a chlorine intermediate; and (iii) allowing at least a portion of the reactant mixture to react via the chlorine intermediate.

3. The process of claim 2, wherein the chlorine intermediate precursor is a chlorine radical precursor, and wherein chlorine intermediate is a chlorine radical.

4. The process of claim 2, wherein the chlorinated catalyst comprises an oxychloride of a rare earth element.

5. The process of claim 4, wherein the oxychloride comprises lanthanum oxychloride (LaOCl).

6. The process of claim 1, wherein the chlorine intermediate precursor is present in the reactant mixture in an amount of from about 0.5 vol. % to about 5 vol. %, based on the total volume of the reactant mixture; and wherein the chlorine intermediate precursor further comprises methyl chloride, methylene chloride, chloroform, carbon tertrachloride, ethyl chloride, 1,2-dichloroethane, trichloroethylene, or combinations thereof.

7. The process of claim 1, wherein the redox agent is present in the catalyst in an amount of from about 1 wt. % to about 25 wt. %, based on the total weight of the catalyst; and wherein the redox agent further comprises tin (Sn), bismuth (Bi), cerium (Ce), or combinations thereof.

8. The process of claim 1, wherein the alkali metal is present in the catalyst in an amount of from about 1 wt. % to about 20 wt. %, based on the total weight of the catalyst; and wherein the alkali metal further comprises potassium (K), rubidium (Rb), cesium (Cs), or combinations thereof.

9. The process of claim 1, wherein the rare earth element is present in the catalyst in an amount of from about 0.5 wt. % to about 10 wt. %, based on the total weight of the catalyst; and wherein the rare earth element further comprises cerium (Ce), praseodymium (Pr), neodymium (Nd), samarium (Sm), dysprosium (Dy), gadolinium (Gd), yttrium (Y), scandium (Sc), or combinations thereof.

10. The process of claim 1, wherein the catalyst comprises one or more oxides of the redox agent; one or more oxides of the alkali metal; one or more oxides of the rare earth element; or combinations thereof.

11. The process of claim 10, wherein the catalyst comprises Na—MnO—$WO_3$—$La_2O_3$, Na—MnO—$La_2O_3$/$Al_2O_3$, Na—MnO—$La_2O_3$/$SiO_2$, or combinations thereof.

12. The process of claim 1, wherein the catalyst further comprises a support; wherein at least a portion of the catalyst contacts, coats, is embedded in, is supported by, and/or is distributed throughout at least a portion of the support; and wherein the support comprises MgO, $Al_2O_3$, $SiO_2$, $ZrO_2$, or combinations thereof.

13. The process of claim 1, wherein the process is characterized by a temperature that is decreased when compared to a temperature of an otherwise similar process conducted (1) with a reactant mixture comprising ethane and oxygen without the chlorine intermediate precursor, and/or (2) with a catalyst comprising a redox agent and an alkali metal without the rare earth element.

14. The process of claim 1, wherein the reacting is characterized by a temperature of less than about 750° C.

15. The process of claim 1, wherein the process is characterized by an ethylene selectivity that is increased when compared to an ethylene selectivity of an otherwise similar process conducted (1) with a reactant mixture comprising ethane and oxygen without the chlorine intermediate precursor, and/or (2) with a catalyst comprising a redox agent and an alkali metal without the rare earth element; and wherein the process is characterized by an ethane conversion that is increased when compared to an ethane conversion of an otherwise similar process conducted (1) with a reactant mixture comprising ethane and oxygen without the chlorine intermediate precursor, and/or (2) with a catalyst comprising a redox agent and an alkali metal without the rare earth element.

16. A process for producing ethylene comprising:
(a) reacting a reactant mixture in a reactor comprising a catalyst to yield a product mixture, wherein:
  i. the reactant mixture comprises ethane, oxygen and a chlorine radical precursor comprising hydrogen chloride (HCl),
  ii. the product mixture comprises ethylene, unreacted ethane, carbon monoxide, and carbon dioxide,
  iii. the catalyst comprises a redox agent comprising manganese (Mn), an alkali metal comprising sodium (Na), and lanthanum (La),
  iv. the Mn is present in the catalyst in an amount of from about 10 wt. % to about 20 wt. %, based on the total weight of the catalyst,
  v. the Na is present in the catalyst in an amount of from about 5 wt. % to about 15 wt. %, based on the total weight of the catalyst,
  vi. the La is present in the catalyst in an amount of from about 1 wt. % to about 5 wt. %, based on the total weight of the catalyst, and
  vii. the reactant mixture is characterized by an ethane to oxygen molar ratio of from about 2:1 to about 6:1; and
(b) recovering at least a portion of the ethylene from the product mixture.

17. The process of claim 16, wherein the reacting in step (a) further comprises (i) contacting at least a portion of the chlorine radical precursor with the catalyst to form a chlorinated catalyst, wherein the chlorinated catalyst comprises lanthanum oxychloride (LaOCl); (ii) allowing at least a portion of the chlorinated catalyst to generate a chlorine radical; and (iii) allowing at least a portion of the reactant mixture to react via the chlorine radical.

18. The process of claim 17, wherein the chlorinated catalyst generates an amount of chlorine radicals that is increased when compared to an amount of chorine radicals generated by an otherwise similar chlorinated catalyst comprising a redox agent and an alkali metal without the La.

19. The process of claim 1 wherein the product mixture comprises less than about 10 mol % carbon dioxide ($CO_2$).

20. The process of claim 1, Wherein the product mixture is characterized by a carbon monoxide to carbon dioxide molar ratio that is increased when compared to a carbon monoxide to carbon dioxide molar ratio of a product mixture produced via an otherwise similar process conducted (1) with a reactant mixture comprising ethane and oxygen without the chlorine intermediate precursor, and/or (2) with a catalyst comprising a redox agent and an alkali metal without the rare earth element.

* * * * *